US008815148B2

(12) United States Patent
Popowski et al.

(10) Patent No.: US 8,815,148 B2
(45) Date of Patent: *Aug. 26, 2014

(54) MAGNESIUM-BASED ALLOY WITH IMPROVED COMBINATION OF MECHANICAL AND CORROSION CHARACTERISTICS

(75) Inventors: Youri Popowski, Geneva (CH); Igor Isakovich Papirov, Kharkov (UA); Vladimir Sergeevitch Shokurov, Kharkov (UA); Anatoliy Ivanovitch Pikalov, Kharkov (UA); Sergey Vladimirovitch Sivtsov, Kharkov (UA)

(73) Assignee: Acrostak Corp. BVI, Winterthur (CH)

( * ) Notice: Subject to any disclaimer, the term of this patent is extended or adjusted under 35 U.S.C. 154(b) by 1163 days.

This patent is subject to a terminal disclaimer.

(21) Appl. No.: 12/293,498

(22) PCT Filed: Mar. 15, 2007

(86) PCT No.: PCT/EP2007/002289
§ 371 (c)(1),
(2), (4) Date: Oct. 21, 2009

(87) PCT Pub. No.: WO2007/107286
PCT Pub. Date: Sep. 27, 2007

(65) Prior Publication Data
US 2010/0049299 A1  Feb. 25, 2010

(30) Foreign Application Priority Data

Mar. 18, 2006 (EP) .................................. 06005592
Apr. 23, 2006 (EP) .................................. 06008368

(51) Int. Cl.
*C22C 23/06* (2006.01)
*C22C 23/00* (2006.01)
*A61F 2/06* (2013.01)

(52) U.S. Cl.
USPC ........................... 420/406; 148/420; 623/1.15

(58) Field of Classification Search
USPC .................. 420/406, 414; 148/420; 623/1.15
See application file for complete search history.

(56) References Cited

U.S. PATENT DOCUMENTS

| 5,059,390 | A  | 10/1991 | Burleigh et al. |
| 5,238,646 | A  | 8/1993  | Tarcy et al. |
| 6,193,817 | B1 | 2/2001  | King et al. |
| 6,395,224 | B1 | 5/2002  | Nishino et al. |
| 6,767,506 | B2 | 7/2004  | Bronfin et al. |
| 6,838,049 | B2 | 1/2005  | Fukuzumi et al. |
| 2004/0098108 | A1 | 5/2004 | Harder et al. |
| 2005/0095166 | A1 | 5/2005 | Saikawa |
| 2005/0129564 | A1 | 6/2005 | Nakamura et al. |
| 2006/0020289 | A1 | 1/2006 | Kuttler |
| 2006/0052864 | A1 | 3/2006 | Harder et al. |

FOREIGN PATENT DOCUMENTS

| DE | 39 22 593 C2 | 1/1991 |
| DE | 102 53 634 A1 | 5/2004 |
| EP | 1 632 255 A2 | 3/2006 |
| JP | 8-23057 B2 | 3/1996 |
| JP | 9-241778 A | 9/1997 |
| JP | 2000-282165 A | 10/2000 |

OTHER PUBLICATIONS

Davis, Joseph R., "Glossary of Metallurgical and Metalworking Terms", Metals Handbook Desk Edition, 1998, ASM International, 2nd Edition, p. 1-218.*
Padfield, T.V., "Metallography and Microstructures of Magnesium and Its Alloys", ASM Handbook, 2004, ASM International, vol. 9, p. 1-14.*
PCT/ISA/210 (International Search Report) dated Aug. 31, 2007, issued in PCT/EP2007/002289.
PCT/ISA/237 (Written Opinion of the International Searching Authority) dated Aug. 31, 2007, issued in PCT/EP2007/002289.

* cited by examiner

*Primary Examiner* — Roy King
*Assistant Examiner* — Caitlin Kiechle
(74) *Attorney, Agent, or Firm* — Buchanan Ingersoll & Rooney

(57) ABSTRACT

Multi-component magnesium-based alloy consisting essentially of about 1.0-15.0 wt. % of scandium, about 0.1-3.0 wt. % of yttrium, about 1.0-3.0 wt. % of rare-earth metal, about 0.1-0.5 wt. % of zirconium. Purity degree of magnesium base is not less of 99.995 wt. %. Impurities of Fe, Ni and Cu do not exceed 0.001 wt. % of everyone, the contents of other impurity in an alloy does not exceed 0.005 wt. %. The alloy demonstrates an improved combination of strength, deformability and corrosion resistance at room temperature. The alloy does not contain harmful and toxic impurities. The alloy can be used in the various practical applications demanding a combination of high strength, deformability and corrosion resistance, preferably in the field of medicine.

28 Claims, No Drawings

MAGNESIUM-BASED ALLOY WITH IMPROVED COMBINATION OF MECHANICAL AND CORROSION CHARACTERISTICS

The given invention generally relates to magnesium-based alloys and, more definitely, to composition and structure of deformable magnesium-based alloys with the improved combination of strength, deformability and corrosion resistance at a room temperature.

Magnesium belongs to the group of light metals and, naturally, is attractive as a constructional material. However it has rather low mechanical characteristics connected with limited quantity of slip planes at plastic deformation in h.c.p. (hexagonal close packing) crystalline structure. Besides magnesium has low corrosion resistance in natural conditions because of strong chemical activity. A unique way of practical using of magnesium is creation of alloys on its basis. Mechanical and corrosion properties of any metals essentially depend on presence into them of other metal elements, which can generate variety intermetallic connections and the solid solutions that may work various influences upon the specified properties. Agency of alloying elements on properties of magnesium-based alloys is well investigated in binary systems, but in multi-component alloys their aggregate effects can appear complex and in advance unpredictable. Therefore the choice of alloying elements and their proportions in an alloy are the controlling factor.

The main alloying elements in industrial magnesium alloys are: aluminum, zinc, lithium, yttrium, manganese, zirconium, rare-earth metals (RE) and their combinations.

Mechanical properties of magnesium alloys, as well as of other metal alloys, are controlled by change: an operating combination of known mechanisms of hardening (solid solution, precipitation strengthening, deformation hardening, grain-boundary hardening, etc.) and mechanisms of plastic deformation as due to alloy building, so also/or by change an alloy condition (temper).

Alloying elements and alloy structure also influence simultaneously its other properties, including corrosion resistance. Corrosion ratio of magnesium and magnesium alloys also strongly depends on magnesium's degree of purity. For example, in 4% water solution of sodium chloride a corrosion ratio of magnesium with purity of 99.9 wt. % is in hundreds times more, than magnesium with purity of 99.99% wt, see Timonova M. A. Korrosia Izaschita magnievix splavov. M. Metallurgija, 1977, 152 p. in Russian.

Besides, some impurities can change a possible solubility range of other impurities. So, addition of aluminum in a magnesium-based alloy increases the influence of other alloying elements on corrosion ratio of alloy [see above]. Distribution of alloying elements and impurities, structure of chemical combination, which they form, affect also the big influence on corrosion ratio of magnesium alloys and their uniformity. Besides corrosion ratio of magnesium alloys depends on a condition of an alloy-deformed, aged, in full or in part annealed etc.

SUMMARY

According to an exemplary aspect, disclosed is an ingot-derived magnesium-based alloy having an improved combination of mechanical and corrosion properties, said alloy consisting essentially of: about 1 to 10 wt. % scandium, up to about 3 wt. % yttrium, about 1 to 3 wt. % rare earth, about 0.1 to 0.5 wt. % zirconium, balance being magnesium with purity not less than 99.995% accordingly to metal impurities.

According to an exemplary aspect, disclosed is an alloy which contains alloying elements with purity not less than 99.99% accordingly to metal impurities.

According to an exemplary aspect, disclosed is an alloy which contains less than about 0.005 wt. % total metal impurities, including up to about 0.001 wt. % iron, up to about 0.001 wt. % nickel and up to about 0.001 wt. % copper.

According to an exemplary aspect, disclosed is an alloy which is free of toxiferous, radioactive and harmful to a living organism elements in concentrations more than 0.0001 wt. % of everyone.

According to an exemplary aspect, disclosed is an alloy whose mechanical and corrosion properties are adjusted by change of scandium concentration in limens from 1 up to 10 wt. %.

According to an exemplary aspect, disclosed is an alloy whose strength characteristics at room temperature (yield stress and ultimate tensile stress) can be enlarged by 20-25% with augmentation of scandium concentration in said alloy from 1 up to 10 wt. %.

According to an exemplary aspect, disclosed is an alloy whose plastic characteristics (elongation, cross-section waist) can be enlarged by 20-25% with augmentation of scandium concentration in said alloy from 1 up to 10 wt. %.

According to an exemplary aspect, disclosed is an alloy whose corrosion ratio in a water solution of sodium chloride at room temperature can be downgraded in 6-8 times by a change of scandium concentration in said alloy from 1 up to 10 wt. %.

According to an exemplary aspect, disclosed is an alloy in wrought condition, whose mechanical and corrosion properties can be additionally adjusted by a change of average grain size of said alloy in the interval 0.1-3 microns.

According to an exemplary aspect, disclosed is an alloy whose strength characteristics (yield stress and ultimate tensile stress) can be enlarged by 25-30% with a decrease of average grain size in said alloy from 0.1 to 3 microns.

According to an exemplary aspect, disclosed is an alloy whose plastic characteristics (elongation, cross-section waist) can be enlarged by 20-25% with a decrease of average grain size in said alloy from 0.1 to 3 microns.

According to an exemplary aspect, disclosed is an alloy which in thermo-mechanical treated condition further are used for tube-, sheets-, rods-, wire manufacturing accordingly to standard production schemes and\or for finished products.

According to an exemplary aspect, disclosed is a stent made of an ingot-derived magnesium-based alloy having an improved combination of mechanical and corrosion properties, said alloy consisting essentially of: about 1 to 10 wt. ° A) scandium, up to about 3 wt. % yttrium, about 1 to 3 wt. % rare earth, about 0.1 to 0.5 wt. % zirconium, balance being magnesium with purity not less than 99.995% accordingly to metal impurities.

According to an exemplary aspect, disclosed is a method for producing a medical product comprising: forming an ingot-derived magnesium-based alloy having an improved combination of mechanical and corrosion properties, said alloy consisting essentially of: about 1 to 10 wt. % scandium, up to about 3 wt. % yttrium, about 1 to 3 wt. % rare earth, about 0.1 to 0.5 wt. % zirconium, balance being magnesium with purity not less than 99.995% accordingly to metal impurities; and configuring a medical product using the alloy.

According to an exemplary aspect, disclosed is a method wherein the medical product is used in stent.

According to an exemplary aspect, disclosed is a method wherein the medical product is used in vivo.

According to an exemplary aspect, disclosed is an alloy whose mechanical and corrosion properties are adjusted by change of scandium concentration in limens from 1 up to 10 wt. %.

According to an exemplary aspect, disclosed is an alloy in wrought condition, whose mechanical and corrosion properties can be additionally adjusted by a change of average grain size of said alloy in the interval 0.1-3 microns.

According to an exemplary aspect, disclosed is an alloy which in thermo-mechanical treated condition further are used for tube-, sheets-, rods-, wire manufacturing accordingly to standard production schemes and\or for finished products.

DETAILED DESCRIPTION

Alloy of the invention are supposed to be used mainly in the field of temperatures 0-50° C. and within the practical applications demanding good deformability and improved corrosion resistance. Therefore the previous development in the field of improvement of mechanical and corrosion properties of magnesium alloys will be considered below only under the specified temperature conditions. Data on improvement of strength, creep resistance and corrosion resistance of magnesium alloys at elevated and high temperatures will be considered only partially, though authors are well familiar with them. It is so, because, though the improved strength of such alloys will be kept and at room temperatures, but their plastic characteristics in these conditions can strongly go down.

Below, at the description of properties of magnesium alloys, the range of temperatures from 0 up to 50° C., and the quantitative contents of alloying elements in percentage on weight will be always implied by, if will not be other special provision.

Plenty of magnesium-based alloys are fabricated now, and their compositions are chosen depending on concrete applications.

The most part of magnesium-based alloys can be conditionally divided into several groups, according to prevailing alloying elements. There are groups of Mg—Li, Mg—Al, Mg—Zn and Mg-RE alloys, where RE—rare-earth metals.

Alloys are also subdivided into classes within the specified groups, according to additional alloying elements. For example, under specification ASTM:

Alloys of type LAE (Mg—Al-RE) are within Mg—Li group;

Alloys of type: AM (Mg—Al—Mn), AZ (Mg—Al—Zn), AE (Mg—Al—P3M) are within of Mg—Al group;

Alloys of type ZK (Mg—Zn—Zr) and alloys ZE (Mg—Zn—P3M) are within Mg—Zn group;

Most known alloys of type WE (Mg—Y—Nd—Zr) are within Mg-RE group.

Alloys of more complex composition, which cannot be carried unequivocally to a concrete class under specification ASTM, are described in various patents. The purpose of their creation is improvement of the certain characteristics of alloys.

Mg—Li eutectic alloys are the most plastic alloys of magnesium (for example, Pat. No. DE 3922593, 1991 Jan. 24). According to binary phase diagram Mg—Li (Freeth W. E., Raynor, G. V., J. Inst. Metals 82, 575-80, 1954), there is an HCP alpha-phase in an alloy at the lithium contents up to 5, 7%, which is peculiar to pure magnesium. At lithium contents more than 10%, the beta-phase, having b.c.c. (body-centered cubic) structure, prevails in an alloy. The possible quantity of sliding systems and, thus, formability of alloys increases in this case. In tensile test at a room temperature elongation of alloy Mg-11Li reaches 39% and UTS—104 MPa (in U.S. Pat. No. 6,838,049).

Lack of magnesium-lithium alloys is low strength and reduction in corrosion resistance of an alloy due to presence of chemically active lithium.

Mg—Li alloys are alloyed in addition for increase of strength and corrosion stability. Aluminum and zinc are often added in Mg—Li alloys for increase of strength and corrosion resistance of them. The addition of 4-10% of aluminum and up to 2% zinc leads to an quite good combination of strength and formability of Mg—Li—Al—Zn alloys.

In Master's Thesis Hsin-Man Lin "Effects of Aluminum Addition on Properties of Magnesium-Lithium Alloys", Date of Defense 2004 Jul. 15, it is shown, that addition 0.6% Al into alloy Mg-9Li can "obviously increase the mechanical strength and corrosion resistance, and maintain the properties of elongation at temperatures below 200° C. and any speeds of deformation".

However presence of aluminum, also as well as zinc, in Mg—Li alloys reduces their formability at room temperature, which is the main advantage of these alloys. Such changes are essential adverse effect of presence of the specified elements in Mg—Li alloys.

There are offered also another combination of alloying elements in alloys on the base of Mg—Li.

In JP Pat. No. 8-23057B yttrium addition is offered for increase in strength of Mg—Li alloy, but presence of one more active element in an alloy reduces, in addition, corrosion resistance of such alloys.

In U.S. Pat. No. 6,838,049 is described "a magnesium alloy formed at a room temperature with excellent resistance of corrosion". Its composition includes from 8.0 up to 11.0% of lithium, from 0.1 up to 4.0% of zinc, from 0.1 up to 4.5% of barium, from 0.1 up to 0.5% Al, and from 0.1 up to 2.5% Ln (a total sum of one or more lanthanides) and from 0.1 up to 1.2% Ca with the balance, which is being Mg and inevitable impurity. Authors consider that "Ba forms an intermetallic compound ($Mg_{17}Ba_2$) with Mg. Because $Mg_{17}Ba_2$ precipitates at a temperature of 634.degree. C. which is close to 588.degree. C., which is the Mg—Li eutectic reaction temperature, but higher than this reaction temperature, it acts as a nucleus when the alpha- and beta-phases precipitate, providing for refinement and uniform dispersion of alpha- and beta-phases".

However, though barium has b.c.c. lattice, but it has a low solubility in Mg and formed intermetallic, which reduce an initial plastic characteristics of Mg—Li alloys.

In U.S. Pat. No. 5,059,390 "A dual-phase magnesium-based alloy consisting essentially of about 7-12% lithium, about 2-6% aluminum, about 0.1-2% rare earth metal, preferably scandium, up to about 2% zinc and up to about 1% manganese" is offered. The alloy exhibits improved combinations of strength, formability and/or corrosion resistance.

In JP Pat. No. 9,241,778 (1997 Sep. 16) the magnesium alloy for use as the constructional material is offered. Alloy contains up to 40% Li and one more additive from the following: up to 10% Al, up to 4% Zn, up to 4% Y, up to 4% Ag and up to 4% RE.

In U.S. Pat. No. 5,238,646 the method of preparation of the alloy having the improved combination of strength, formability and corrosion resistance is offered. The specified alloy includes: approximately 7-12% of lithium; approximately 2-7% of aluminum; approximately 0.4-2% RE; approximately up to 2% of zinc; and approximately up to 1% of manganese, balance magnesium and impurity. Purity of magnesium taken for a basis of an alloy is 99.99%. Authors ranked yttrium and scandium also to group of rare earth metal. Though they have an identical structure of external electronic shells of atoms with metals of RE group and similarity of some chemical properties, but they shell be distinguished from RE, according to Standard ASTM, in their differing characteristics for alloys.

In JP Pat. No. 2000 282165 Mg—Li alloy with the improved corrosion resistance is offered. The alloy contains up to 10.5% Li and magnesium with concentration of iron<=50 p.p.m., which can be achieved "by carrying out the melting of the alloy in a crucible coated with chromium or chromium oxide".

Mg—Al alloys (classes AM, AZ and AE) are the most widespread in practice group of magnesium alloys. However, though they also show the better corrosion resistance and higher strength, than Mg—Li alloys, but they are much less plastic properties.

One of methods of corrosion resistance increasing of magnesium alloys is reduction of a contents level of Fe, Ni and Cu. According to L. Duffy (Materials World, vol. 4, pp. 127-30, 1996), corrosion ratio of alloy AZ91E (salt fog tests) is in 100 times less, than for alloy AZ91C, owing to higher purity (0.1% Cu, 0.01% Ni, 0.3% max the others—in alloy AZ91C and 0.015% Cu, 0.001% Ni, 0.005% Fe, 0.3% max the others—in alloy AZ91E).

In U.S. Pat. No. 2005 0,129,564 it is offered the alloy containing: of 10 to 15% Al, 0.5 to 10% Sn, 0.1 to 3% Y, and 0.1 to 1% Mn, the balance being Mg and inevitable impurities.

In U.S. Pat. No. 6,395,224 the alloy, which includes magnesium as a main component, boron of 0.005% or more, manganese of 0.03 to 1%, and substantially no zirconium or titanium is offered. This magnesium alloy may further include aluminum of 1 to 30% Al and/or zinc of 0.1 to 20%. Because of appropriate amounts of boron and manganese contained in the magnesium alloy, the grain of the magnesium alloy is refined.

In U.S. Pat. No. 2005 0,095,166 it is offered "Heat resistant magnesium alloy for casting", which includes 6-12% of aluminum, 0.05-4% of calcium, 0.5-4% of rare earth elements, 0.05-0.50% of manganese, 0.1-14% of tin, balance are magnesium and inevitable impurities. Data about plastic characteristics of an alloy at room temperatures are not resulted.

Among Mg—Zn alloys are the most known: alloys of class ZK (magnesium-zinc-zirconium), having good durability and plasticity at a room temperature; alloys of class ZE (magnesium-zinc-RE), having average durability; alloys of class ZH (magnesium-zinc-thorium), having high room-temperature yield strength in aged condition (T5). The magnesium alloys, containing thorium, are not made now, because of their weak radio-activity.

In U.S. Pat. No. 2001 6,193,817 it is offered a magnesium base alloy for high pressure die casting (HPDC), providing good creep and corrosion resistance, comprises: at least 91% of magnesium; 0.1 to 2% of zinc; 2.1 to 5% of a rare earth metal component; 0 to 1% of calcium.

Alloys of type WE (Mg—Y—Nd—Zr) are the most known among alloys Mg with RE. These alloys possess quite good formability and the increased corrosion resistance. According to the specification of the manufacturer (Magnesium Elektron Ltd., Manchester, England) elongation of alloy ELEKTRON WE43 CASTINGS can achieve 17% at a room temperature, and corrosion ratio is equal 0.1-0.2 mg\cm$^2$\day (ASTM B117 salt spray test) or 0.1 mg\cm$^2$\day (sea water immersion test). However, deformability of this alloy is insufficient in many cases, and the experimental dispersion of mechanical characteristics of WE43 ingots is very great: elongation 2-17% (average value is 7%, data of the manufacturer on the base of 215 samples). Deformed (extruded, forget) and thermo-threatened alloy WE 43 shows more stable, but lower plasticity at a room temperature—up to 10% (condition T5, T6).

Various changes of Mg-RE alloys composition are offered for increase of its operating ability.

In U.S. Pat. No. 6,767,506 2004 Jul. 27 it is offered "High temperature resistant magnesium alloys", containing at least 92% magnesium, 2.7 to 3.3% neodymium, 0.0 to 2.6% yttrium, 0.2 to 0.8% zirconium, 0.2 to 0.8% zinc, 0.03 to 0.25% calcium, and 0.00 to 0.001% beryllium. The alloy may additionally contain up to 0.007 iron, up to 0.002% nickel, up to 0.003% copper and up to 0.01 silicon and incidental impurities.

Interest to WE-type alloys, as to a constructional material of vessel stents, has increased last years. For example, in U.S. Pat. No. 2004 098,108 it is offered to make vascular endoprostheses, comprising a carrier structure, which contains a metallic material. This metallic material contains a magnesium alloy of the following composition: magnesium: >90%, yttrium: 3.7-5.5%, rare earths: 1.5-4.4% and balance: <1%. In essence, this composition corresponds to alloy WE43. However, because of insufficient plasticity of such alloy, authors had simultaneously to offer a new stent design, which provides its working capacity at the lowered plastic characteristics of the offered alloy.

Mechanical characteristics (tensile test, room temperature) and corrosion ratio of some most widespread magnesium-based alloys, taken of various accessible sources are resulted in Table 1.

TABLE 1

| Alloy | YS, MPa | UTS, MPa | Elongation, % | Corrosion ratio | Treatment, condition |
|---|---|---|---|---|---|
| WE43 | 195 | 280 | 10 | 0.1 mg/cm$^2$/day (sea water immersion) 0.1-0.2 mg/cm$^2$/day ASTM B 117 salt spray test | Extruded, T5 |
| WE43 | 180 | 300 | 10 | — | Forging, T5 |
| WE43 | 190 | 270 | 10 | 2.6 mg/cm$^2$/day * | Extruded, T6 |
| AZ 91D | 150 | 230 | 3 | <0.13 mg/cm$^2$/day ASTM B 117 salt spray test | Ingot, F |
| AZ 91E | 90 | 275 | 15 | | Ingot, T4 |
| AM 60B | 130 | 220 | 6-8 | <0.13 mg/cm$^2$/day ASTM B 177 salt spray test | Ingot, F |
| AZ 61 | 230 | 310 | 16 | | Deformed, F |
| ZK 60 | 295 | 360 | 12 | | Deformed, T5 |
| AM 160 | 130 | 220 | 8 | | Ingot, F |
| Mg—11Li | — | 105 | 39 | | Ingot, F |
| Alloy of invention, Example 1 | 240 | 320 | 25 | 2.1 mg/cm$^2$/day * | Deformed, annealed (H2) |
| Alloy of invention, Example 2 | 210 | 290 | 29 | 2.9 mg/cm$^2$/day * | Deformed, annealed (H2) |

Tests for corrosion behavior were carried out by the special technique: in a stream of 0.9% water solution of sodium chloride. Speed of stream was 50 m\min. Corrosion ratio was determined on loss of sample's weight and through quantity of magnesium, passed into a solution washing specimen. The data of measurements were averaged. Such testing scheme allows continuously washing off products of corrosion from sample's surface which, for example, deform results of corrosion ratio studying by a method of measurement of sample's weight loss.

Characters in titles of alloys designate: A—aluminum, E—the rare earth (RE), K—zirconium, L—lithium, M—manganese, W—yttrium, Z—zinc, and figures—the contents of an alloying elements approximated to an integer in percentage.

Table 1 shows that various magnesium alloys have different combinations of mechanical and corrosion characteristics. One has higher strength, others are less strength, but are more deformable. However, for responsible applications, it is desirable to combine high strength and high plasticity with preservation of sufficient level of corrosion resistance.

The purpose of the present invention is creation of new magnesium-based alloy having improved (in comparison with existing) combination of strength and plasticity at preservation of low corrosion ratio, peculiar to alloys of WE- and AZ-types. For example, it is desirable to create an alloy having yield stress (YS) more 200 MPa, tensile strength about 300 MPa and more, elongation more than 22% and corrosion ratio about of 0.1 mg\cm$^2$\day (sea water immersion test) at a room temperature.

On the basis of available data about the influence of various alloying elements and their compounds (quantity, condition, distribution, etc.) on magnesium properties and the carried out own experiments, authors have accepted following preconditions for development of an offered alloy.

1. The magnesium taken as a basis of an alloy should have high purity. The total contents of impurities should no be more than 0.005%, without taking into account contents of Fe, Ni and Cu. The contents of these elements, affect the most adverse influence on corrosion characteristics of magnesium, should be limited no more than 0.001% of everyone.

2. The alloy should contain alloying elements in the quantities, which are not essentially exceeding their solubility in solid magnesium, according to known binary phase diagrams.

3. Purity of alloying elements should not be worse than 99.98% (only metal impurities are considered).

4. Authors have chosen basic alloying elements, which appreciably improve one of characteristics of alloy in considered combination (strength, plasticity, corrosion resistance) and which influence minimally unfavorably on other alloy properties of invention.

5. For use in medical purposes, the alloy of invention should not contain, in appreciable quantities, the elements that affect adverse influence on human's or animal's organism (Zn, Th, Sr, Cd, Al, etc).

6. It is necessary to add in alloy the elements that affect modifying influence (grain-refining) on its structure and providing grain size in initial ingot no more 10 microns.

7. For additional (besides an alloying) improvement in combination of mechanical and corrosion characteristics of offered alloy, it is suggested to use it in ultra fine-grained condition with the average grain size no more than 3 microns. The specified grain structure may be created by processing of an initial ingot or preliminary extruded slab with application of developed by authors method of programmed intensive plastic deformation in a combination with programmed heat treatment [Physitcheskoe metallovedenie beryllium, I. Papirov, G. Tikhinsky, 1968, Atomizdat, Moscow, in Russian]. Methods of pressure processing of preform should be applied for this purpose, which will be providing prevalence of torsional or shear stresses in a handled material.

On the basis of the aforesaid authors have chosen following alloying elements for magnesium-based alloy as the preferred embodiment(s) of the given invention.

Scandium has a limit of solubility in solid magnesium about 29%. According to laboratory findings of authors, addition of scandium into magnesium within the limits of up to 8% provides creation of solid solution Mg—Sc that increases its plasticity and strength. In the interval of scandium concentration from 3 up to 8% corrosion ratio of Mg—Sc alloy in water solution of sodium chloride increases slightly. Precipitation of Mg—Sc phase is possible during high-temperature processing of magnesium alloys with the big contents of scandium. However, very thin intermetallic bond in the form of the plates, formed in a direction <1120> in a basal plane, is distributed non-uniformly and do not make any hardening at a room temperature when the main mechanism of deformation is basic sliding [Buch F., Mordike B.: *Microstructure, Mechanical Properties and Creep Resistance of Binary Magnesium Scandium Alloys*. In: Magnesium 97 (Eds. Aghion, E., Eliezer, D.), MRI, Beer Sheva 1998, p. 163-168].

Besides scandium also is the strong modifier grain structure of magnesium ingots.

Yttrium has the limit of solubility in magnesium about 2% at room temperature. Addition up to 3% of yttrium into magnesium increases strength of an alloy without essential reduction in its plasticity and corrosion resistance.

Rare earth (RE) metals influence on properties of magnesium alloys depends on their solubility in it and their melt point. Solubility RE in solid magnesium changes from practically zero (La) up to 7 percent (Lu). Metals from group with nuclear numbers from 64 (Gd) up to 71 (Lu) have melting temperatures and limits of solubility in magnesium higher, than metals of cerium group. Introduction up to 3% refractory RE in a magnesium alloy raises creep and corrosion resistance of an alloy, and reduces micro porosity of multi-component alloy at its melting.

Zirconium, as is well-known, is a basic element, which crushes grain size in magnesium alloys during an ingot production. The fine-grained ingot is easier exposed to preliminary and subsequent deformation.

In accordance with the foregoing objectives, as preferable embodiments, authors offer the following magnesium-based alloy having the improved combination of mechanical and corrosion characteristics at room temperature. Alloy consists essentially of: magnesium base with purity not less 99.995%, scandium from 1 up to 10%, preferable 2.5-6%, yttrium from 0.1 up to 3%, preferable 2-2.5%, rare earth from 1 up to 3%, zirconium from 0.1 up to 0.5%, preferable 0.3-0.4%. Contents Fe, Ni and Cu do not exceed 0.001% of everyone, the total contents of incidental elements and impurities do not exceed 0.005%.

Alloy of the specified composition is received by direct fusion of magnesium with preliminary prepared master alloy from the specified alloying elements in high-frequency induction furnace in atmosphere of high purity argon and in high purity graphite crucible. Melt is poured out in cooled steel mold with a special daubing by a method of bottom teem.

The prepared ingot further is subjected to pressure treatment by the developed by authors method of programmed intensive plastic deformation (for example, by different-channel angular extrusion) at temperatures 250-350° C. in combination with programmed heat treatment. At achievement of micro-hardness Hμ more than 110 kg/mm$^2$, preform is subjected to an annealing at temperature 270-320° C.

Preform prepared by the above-stated method, further is subjected to usual industrial schemes reception of sheets, rods, wire, tubes, etc. for produce final products.

For example the alloy material is well qualified for stents. The alloy material has the capability of a desired deformation regarding to a specific application. Furthermore the grain size is adjustable for tuning the strength characteristics.

EXAMPLES OF PREFERRED EMBODIMENTS

Example 1

Alloy consists essentially of: magnesium with purity of 99.997% with addition of 4.2% scandium, 2.4% yttrium, 3.0% the rare earth, 0.4% zirconium. Contents Fe, Ni and Cu were not exceed 0.001% of everyone, the contents of incidental elements and impurities do not exceed 0.005%.

The alloy was received by direct fusion of magnesium with preliminary prepared master alloy from the specified elements in high-frequency induction furnace in an atmosphere of high purity argon and in high purity graphite crucible.

For full dissolution of all components, alloy was stood in crucible at temperature 720° C. within 30 minutes and then was poured out in cooled steel mold with a special daubing by a method of bottom teem.

The received ingot (diameter of 50 mm) was extruded at temperature 340° C. with an extrusion ratio of 3:1.

The received semi-finished product has been subjected to deformation by different-channel angular extrusion at temperature 320° C., number of cycles of extrusion—12, with intermediate annealing at temperature 275° C. through 2-3 cycles (at achievement of micro-hardness $H_\mu$ of 110 kg/mm$^2$).

Samples have been cut out from the received extrudate for tensile test at room temperature and tests for corrosion behavior (in a stream of 0.9% water solution of sodium chloride. Speed of stream was 50 m\min).

Test Results:

Mechanical properties (after annealing at temperature 320° C. within one hour): YS=240 MPa, UTS=320 MPa, elongation=25%.

Corrosion ratio (it is obtained by measurement of weight loss of specimens and quantitative definition of the magnesium, which has passed in a solution, through the fixed time intervals)—2.1 mg/cm$^2$/day.

Results of tests show that the alloy of the invention with the specified composition has the best combination of mechanical and corrosion properties in comparison with the most widespread industrial alloys of magnesium (see Tabl. 1).

Example 2

The ingot on the basis of magnesium with purity of 99.995%, with addition of 10.0% scandium, 1.4% yttrium, 2.0% of rare earth (mainly—gadolinium) and 0.5% zirconium was received by the method specified in an example 1.

Then the ingot had been subjected to deformation by alternation of cycles extrusion with extrusion ratio 2.5:1 and swage out till initial diameter (one cycle) at temperatures 300-340° C., number of cycles—5, with intermediate annealing at temperature 275° C.

Samples have been cut out from the received preparation for mechanical tests and tests for corrosion (in a stream of 0.9% water solution of sodium chloride. Speed of stream was 50 m\min).

Test Results:

Mechanical properties (after annealing at temperature 290° C. within one hour): YS=210 MPa, UTS=290 MPa, elongation=29%. Corrosion ratio (in stream)—2.9 mg/cm$^2$/day.

Results of tests show that the alloy of the invention of the specified structure has the best combination of deformability and corrosion properties at satisfactory strength in comparison with the most widespread industrial alloys of magnesium (see table 1).

The invention claimed is:

1. An ingot-derived magnesium-based alloy having an improved combination of mechanical and corrosion properties, said alloy consisting essentially of: about 1 to 10 wt. % scandium, up to about 3 wt. % yttrium, about 1 to 3 wt. % rare earth metals other than scandium and yttrium, about 0.1 to 0.5 wt. % zirconium, balance being magnesium with purity not less than 99.995% accordingly to metal impurities.

2. The alloy of claim 1, wherein the alloying elements have a purity not less than 99.99% accordingly to metal impurities.

3. The alloy of claim 1, which further contains less than about 0.005 wt. % total metal impurities, including up to about 0.001 wt. % iron, up to about 0.001 wt. % nickel and up to about 0.001 wt. % copper.

4. The alloy of claim 3, which further contains not more than 0.0001 wt. % of each of toxiferous, radioactive and harmful to a living organism elements.

5. The alloy of claim 1, which further contains not more than 0.0001 wt. % of each of toxiferous, radioactive and harmful to a living organism elements.

6. The alloy of claim 5, whose mechanical and corrosion properties are adjusted by change of scandium concentration in limens from 1 up to 10 wt. %.

7. The alloy of claim 1, wherein the alloy further contains not more than 0.0001 wt. % of each of aluminum, cadmium, strontium, thorium and zinc.

8. The alloy of claim 7, wherein the alloy further contains up to about 0.001 wt. % iron.

9. The alloy of claim 1, whose mechanical and corrosion properties are adjusted by change of scandium concentration in limens from 1 up to 10 wt. %.

10. The alloy of claim 9, whose strength characteristics at room temperature are enlarged by 20-25% with augmentation of scandium concentration in said alloy from 1 up to 10 wt. %.

11. The alloy of claim 10, wherein the strength characteristics include yield stress and ultimate tensile stress.

12. The alloy of claim 9, whose plastic characteristics are enlarged by 20-25% with augmentation of scandium concentration in said alloy from 1 up to 10 wt. %.

13. The alloy of claim 12, wherein the plastic characteristics include elongation, cross-section waist.

14. The alloy of claim 9, whose corrosion ratio in a water solution of sodium chloride at room temperature is downgraded by 6-8 times by a change of scandium concentration in said alloy from 1 up to 10 wt. %.

15. The alloy of claim 9, which is in a thermo-mechanical treated condition, and is used for tube-, sheets-, rods-, wire manufacturing and/or for finished products.

16. The alloy of claim 9, wherein the alloy is in a wrought condition, wherein mechanical and corrosion properties of the alloy are additionally adjusted by a change of average grain size of said alloy in the interval 0.1-3 microns.

17. The alloy of claim 1, wherein the alloy is in a wrought condition, wherein mechanical and corrosion properties of the alloy are additionally adjusted by a change of average grain size of said alloy in the interval 0.1-3 microns.

18. The alloy of claim 17, whose strength characteristics are enlarged by 25-30% with a decrease of average grain size in said alloy from 0.1 to 3 microns.

19. The alloy of claim 18, wherein the strength characteristics include yield stress and ultimate tensile stress.

20. The alloy of claim 17, whose plastic characteristics are enlarged by 20-25% with a decrease of average grain size in said alloy from 0.1 to 3 microns.

21. The alloy of claim 20, wherein the plastic characteristics include elongation, cross-section waist.

22. The alloy of claim 17, which is in a thermo-mechanical treated condition, and is used for tube-, sheets-, rods-, wire manufacturing and/or for finished products.

23. Stent made of an ingot-derived magnesium-based alloy having an improved combination of mechanical and corrosion properties, said alloy consisting essentially of: about 1 to 10 wt. % scandium, up to about 3 wt. % yttrium, about 1 to 3 wt. % rare earth metals other than scandium and yttrium, about 0.1 to 0.5 wt. % zirconium, balance being magnesium with purity not less than 99.995% accordingly to metal impurities.

24. Method for producing a medical product comprising:
forming an ingot-derived magnesium-based alloy having an improved combination of mechanical and corrosion properties, said alloy consisting essentially of: about 1 to 10 wt. % scandium, up to about 3 wt. % yttrium, about 1 to 3 wt. % rare earth metals other than scandium and yttrium, about 0.1 to 0.5 wt. % zirconium, balance being magnesium with purity not less than 99.995% accordingly to metal impurities; and
configuring a medical product using the alloy.

25. Method according to claim 24, wherein the medical product is used in a stent.

26. Method according to claim 24, wherein the medical product is used in vivo.

27. An ingot-derived magnesium-based alloy having an improved combination of mechanical and corrosion properties, said alloy consisting essentially of:
about 1 to 10 wt. % scandium,
up to about 3 wt. % yttrium,
about 1 to 3 wt. % rare earth metals other than scandium and yttrium,
about 0.1 to 0.5 wt. % zirconium,
up to about 0.001 wt. % iron,
up to about 0.001 wt. % nickel,
up to about 0.001 wt. % copper,
not more than 0.0001 wt. % of each of toxiferous, radioactive and harmful to a living organism elements,
less than 0.005% total metal impurities,
balance being magnesium.

28. The alloy of claim 27, wherein the alloy further contains not more than 0.0001 wt. % of each of aluminum, cadmium, strontium, thorium and zinc.

* * * * *